(12) United States Patent
Cohen et al.

(10) Patent No.: US 10,258,449 B2
(45) Date of Patent: *Apr. 16, 2019

(54) HERNIA REPAIR DEVICE AND METHOD

(71) Applicant: Covidien LP, Mansfield, MA (US)

(72) Inventors: Matthew D. Cohen, Berlin, CT (US);
Michael Prescott, Hamden, CT (US)

(73) Assignee: Covidien LP, Mansfield, MA (US)

( * ) Notice: Subject to any disclaimer, the term of this patent is extended or adjusted under 35 U.S.C. 154(b) by 255 days.

This patent is subject to a terminal disclaimer.

(21) Appl. No.: 15/275,627

(22) Filed: Sep. 26, 2016

(65) Prior Publication Data

US 2017/0007387 A1   Jan. 12, 2017

Related U.S. Application Data

(63) Continuation of application No. 14/345,792, filed as application No. PCT/US2012/058237 on Oct. 1, 2012, now Pat. No. 9,492,261.

(60) Provisional application No. 61/541,645, filed on Sep. 30, 2011.

(51) Int. Cl.
*A61B 17/04* (2006.01)
*A61F 2/00* (2006.01)
*A61B 17/06* (2006.01)

(52) U.S. Cl.
CPC ............. *A61F 2/0063* (2013.01); *A61B 17/06* (2013.01); *A61B 17/0493* (2013.01); *A61B 2017/06176* (2013.01); *A61F 2220/0016* (2013.01); *A61F 2220/0075* (2013.01)

(58) Field of Classification Search
CPC ................ A61B 17/0493; A61B 17/06; A61B 17/06004; A61B 17/06166; A61B 2017/06176; A61F 2/0063; A61F 2002/0068; A61F 2002/0072; A61F 2220/0016; A61F 2220/0075

See application file for complete search history.

(56) References Cited

U.S. PATENT DOCUMENTS

| | | | |
|---|---|---|---|
| 2,671,444 | A | 3/1954 | Pease, Jr. |
| 4,865,026 | A | 9/1989 | Barrett |
| 5,116,357 | A | 5/1992 | Eberbach |
| 5,634,931 | A | 6/1997 | Kugel |
| 5,879,366 | A | 3/1999 | Shaw et al. |
| 5,972,022 | A | 10/1999 | Huxel |
| 6,270,517 | B1 | 8/2001 | Brotz |

(Continued)

FOREIGN PATENT DOCUMENTS

| | | |
|---|---|---|
| EP | 2386252 A1 | 11/2011 |
| FR | 2914178 A1 | 10/2008 |

(Continued)

OTHER PUBLICATIONS

Chinese office action issued in corresponding application No. 201280047937.3 dated Dec. 18, 2015.

(Continued)

*Primary Examiner* — Ryan J. Severson (57) ABSTRACT

A hernia repair device includes a mesh configured figured to extend across a tissue defect and a plurality of filaments coupled to the mesh. The filaments are coupled to the mesh in proximity of an outer periphery thereof and extend from a central portion of the mesh. Each filament includes a plurality of barbs disposed along at least a portion of the length thereof. Each filament further includes a needle disposed at a free end thereof.

19 Claims, 4 Drawing Sheets

(56) References Cited

U.S. PATENT DOCUMENTS

| | | |
|---|---|---|
| 6,436,030 B2 | 8/2002 | Rehil |
| 6,669,735 B1 | 12/2003 | Pelissier |
| 6,736,823 B2 | 5/2004 | Darois et al. |
| 6,790,213 B2 | 9/2004 | Cherok et al. |
| 7,021,316 B2 | 4/2006 | Leiboff |
| 7,094,261 B2 | 8/2006 | Zotti et al. |
| 7,413,569 B2 | 8/2008 | Sogaard-Andersen |
| 7,566,337 B2 | 7/2009 | Sogaard-Andersen et al. |
| 7,594,921 B2 | 9/2009 | Browning |
| 7,824,420 B2 | 11/2010 | Eldridge et al. |
| 8,500,759 B2 | 8/2013 | Koyfman et al. |
| 8,579,922 B2 | 11/2013 | Glick et al. |
| 8,932,328 B2 | 1/2015 | Megaro et al. |
| 8,945,235 B2 | 2/2015 | Horton et al. |
| 9,265,595 B2 | 2/2016 | Cohen |
| 9,492,261 B2 | 11/2016 | Cohen et al. |
| 2001/0049539 A1 | 12/2001 | Rehil |
| 2002/0103494 A1 | 8/2002 | Pacey |
| 2003/0130745 A1 | 7/2003 | Cherok et al. |
| 2003/0171823 A1 | 9/2003 | Zotti et al. |
| 2003/0212460 A1 | 11/2003 | Darois et al. |
| 2004/0073257 A1 | 4/2004 | Spitz |
| 2004/0172048 A1 | 9/2004 | Browning |
| 2004/0181288 A1 | 9/2004 | Darois et al. |
| 2004/0215219 A1 | 10/2004 | Eldridge et al. |
| 2005/0159777 A1 | 7/2005 | Spitz |
| 2006/0235543 A1 | 10/2006 | Sogaard-Andersen |
| 2006/0276908 A1 | 12/2006 | Sogaard-Andersen et al. |
| 2008/0033461 A1 | 2/2008 | Koeckerling et al. |
| 2008/0082113 A1 | 4/2008 | Bishop et al. |
| 2008/0167729 A1 | 7/2008 | Nelson et al. |
| 2009/0082792 A1 | 3/2009 | Koyfman et al. |
| 2009/0228021 A1 | 9/2009 | Leung |
| 2010/0016872 A1 | 1/2010 | Bayon et al. |
| 2010/0189764 A1 | 7/2010 | Thomas et al. |
| 2010/0222794 A1 | 9/2010 | Browning |
| 2010/0241145 A1 | 9/2010 | Cook |
| 2010/0274283 A1 | 10/2010 | Kirsch et al. |
| 2010/0286716 A1 | 11/2010 | Ford et al. |
| 2011/0054522 A1 | 3/2011 | Lindh, Sr. et al. |
| 2011/0082478 A1 | 4/2011 | Glick et al. |
| 2011/0130774 A1 | 6/2011 | Criscuolo et al. |
| 2011/0282386 A1 | 11/2011 | Friedrich et al. |
| 2012/0046675 A1 | 2/2012 | Bishop et al. |
| 2012/0101522 A1 | 4/2012 | Megaro et al. |
| 2013/0066423 A1 | 3/2013 | Bishop et al. |
| 2013/0172915 A1 | 7/2013 | Thomas et al. |
| 2013/0190785 A1 | 7/2013 | Koyfman et al. |
| 2014/0025093 A1 | 1/2014 | Horton et al. |
| 2014/0221736 A1 | 8/2014 | Cohen |
| 2014/0257027 A1 | 9/2014 | Palmisano et al. |
| 2015/0018851 A1 | 1/2015 | Francois et al. |
| 2015/0073473 A1 | 3/2015 | Broom et al. |
| 2015/0100072 A1 | 4/2015 | Megaro et al. |
| 2015/0148824 A1 | 5/2015 | Horton et al. |
| 2015/0157437 A1 | 6/2015 | Cohen et al. |
| 2015/0209127 A1 | 7/2015 | Cohen |
| 2015/0327988 A1 | 11/2015 | Bishop et al. |

FOREIGN PATENT DOCUMENTS

| | | |
|---|---|---|
| WO | 2008042992 A2 | 4/2008 |
| WO | 2008055028 A1 | 5/2008 |
| WO | 2009075933 A1 | 6/2009 |

OTHER PUBLICATIONS

European Search Report from corresponding EP Application No. 12834873.7 dated Jun. 25, 2015.

International Search Report for PCT/US12/58237 date of completion is Jan. 29, 2013 (3 pages).

Patent Examination Report issued in corresponding application No. 2012315583 dated Apr. 29, 2016.

Japanese Office Action dated Jun. 30, 2016 in corresponding JP Application No. 2014-533465.

Chinese Third Office Action corresponding to counterpart Int'l Appln. No. CN 201280047937.3 dated Mar. 21, 2017.

Canadian Office Action dated Jun. 13, 2018, in CA Appln. No. 2,849,105.

HERNIA REPAIR DEVICE AND METHOD

CROSS-REFERENCE TO RELATED APPLICATIONS

This application is a continuation of U.S. patent application Ser. No. 14/345,792 filed Oct. 1, 2012, which is a National Stage Application of PCT/US12/58237 under 35USC § 371 (a), which claims priority of U.S. Provisional Patent Application Ser. No. 61/541,645 filed Sep. 30, 2011, and the disclosures of each of the above-identified applications are hereby incorporated by reference in their entirety.

BACKGROUND

Technical Field

The present disclosure relates to hernia repair devices and, more particularly, to surgical mesh prosthetics for use in hernia repair.

Background of Related Art

Wound closure devices, such as sutures, filaments, and staples, as well as other repair devices, such as mesh or patch reinforcements, are frequently used to repair tissue defects, e.g., herniated tissue, and other damaged and/or diseased tissue. For example, in the case of hernias, a surgical mesh or patch is commonly used to reinforce the abdominal wall. The surgical mesh is generally sized to extend across the defect and is adapted to flex or bend in order to conform to the abdominal wall. The surgical mesh is typically held in place by adhering, suturing or stapling the mesh to the surrounding tissue.

However, difficulties may arise during the course of a hernia repair procedure, particularly with regard to properly positioning the surgical mesh and/or securely affixing the mesh to surrounding tissue. These difficulties are often attributed to anatomical spatial constrains and/or reduced, or limited, access to the surgical site. Improper positioning or affixing of the mesh may result in re-herniation, dislodging or repositioning of the surgical mesh relative to tissue and/or viscera entering the defect.

U.S. Pat. No. 7,021,316 discloses a device and method for tacking a prosthetic screen to the abdominal wall. In particular, the tacking device includes a barbed filament having a foot at one end and a loop at the other end. In use, one or more tacking devices are secured to the screen. Thereafter, the screen is positioned within the abdominal cavity about the defect. Next, a filament passer is used to penetrate the abdominal wall adjacent the loop portion of the tacking device. The filament passer is engaged to the loop of the tacking device and is pulled back through the abdominal wall to pull the barbed filament through the abdominal wall. This process is then repeated to secure each of the tacking devices within tissue.

SUMMARY

In accordance with one embodiment of the present disclosure, a hernia repair device is provided. The hernia repair device includes a mesh configured to extend across a tissue defect and a plurality of filaments coupled to the mesh. The filaments are coupled to the mesh in proximity of an outer periphery thereof and extend from a central portion of the mesh. Each filament includes a plurality of barbs disposed along a portion or the entire length thereof. Each filament further includes a needle disposed at a free end thereof.

In one embodiment, the mesh includes a first annular support member coupled thereto in proximity of the outer periphery thereof. The mesh may also include a second a second annular support member coupled thereto toward the central portion thereof. Further, the filaments may be coupled to the first annular support member and may be configured to extend radially inwardly along the mesh toward the second annular support member such that each filament extends through an aperture defined by the second annular support member.

In another embodiment, the filaments provide radial structural support to the mesh. Further, the filaments may be substantially equally-spaced about the mesh, or may be disposed in any other suitable configuration.

In yet another embodiment, each filament includes two or more support strands coupled thereto such that each filament is coupled to the mesh in two or more attachment positions.

In still another embodiment, a removable protective sheath is disposed about the needle of each of the filaments to protect against injury and/or damage during handling of the hernia repair device. The removable protective sheath of each filament may be configured to extend about the barbed portion of the filament to further protect against injury and/or damage.

In still yet another embodiment, the mesh is configured to be resiliently deformable to facilitate insertion of the mesh through the tissue defect. The mesh may further be configured to conform to the anatomy of the tissue defect and surrounding tissue.

In another embodiment, the barbs disposed along the filaments are angled relative to the filaments such that each filament is configured to pass through tissue in a first direction but is inhibited from passing through tissue in a second, opposite direction.

A method for repairing a tissue defect is also provided in accordance with the present disclosure. The method includes providing a hernia repair device according to any of the embodiments mentioned above. The method further includes inserting the mesh through a tissue defect such that the mesh extends across the tissue defect and such that the filaments extend proximally through the tissue defect and independently and incrementally advancing each of the filaments through tissue surrounding the tissue defect to secure the mesh in a desired position relative to the tissue defect.

In embodiments where the hernia repair device includes removable protective sheaths, the removable protective sheaths are removed from the filaments prior to advancing the filaments through tissue.

In one embodiment, each filament is advanced through tissue proximally and in a direction towards an attachment position of the filament to the mesh.

In another embodiment, the mesh is resiliently deformed during insertion through the tissue defect to facilitate passage of the mesh through the tissue defect.

BRIEF DESCRIPTION OF THE DRAWINGS

Various embodiments of the present disclosure are described herein with reference to the drawings wherein.

DETAILED DESCRIPTION

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 1:
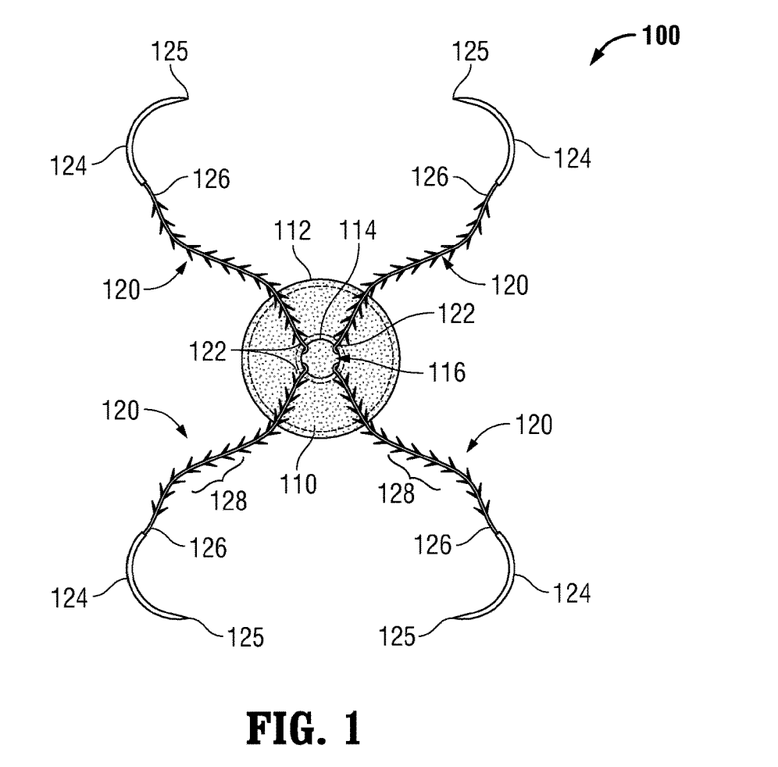
FIG. 1 is a top view of one embodiment of a hernia repair device provided in accordance with the present disclosure.
Figure 2:
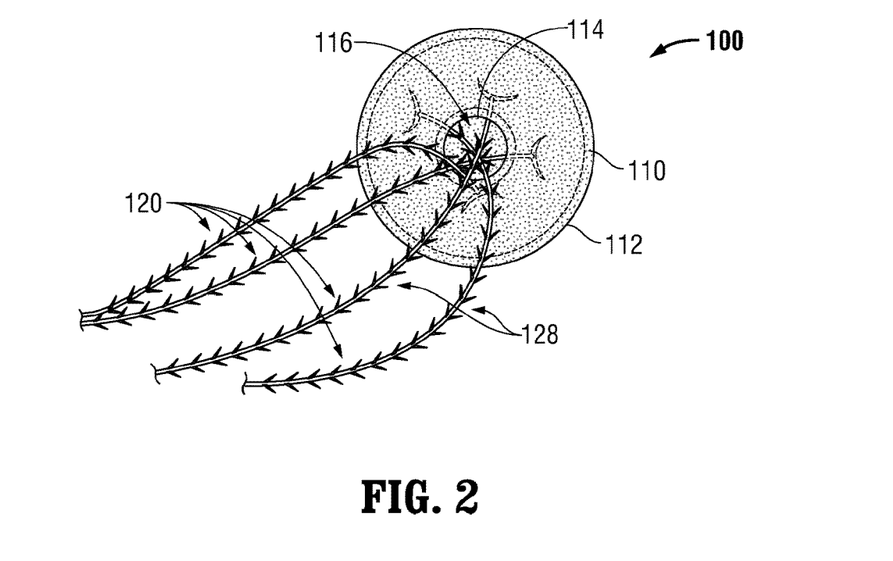
FIG. 2 is a top view of another embodiment of a hernia repair device provided in accordance with the present disclosure.
Figure 3:
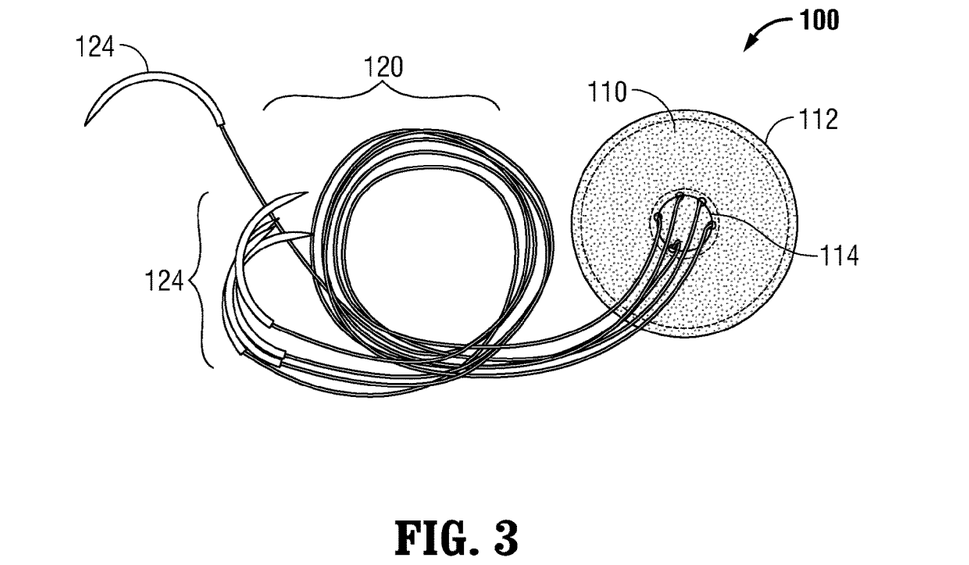
FIG. 3 is a top view of yet another embodiment of a hernia repair device provided in accordance with the present disclosure.
Figure 6:
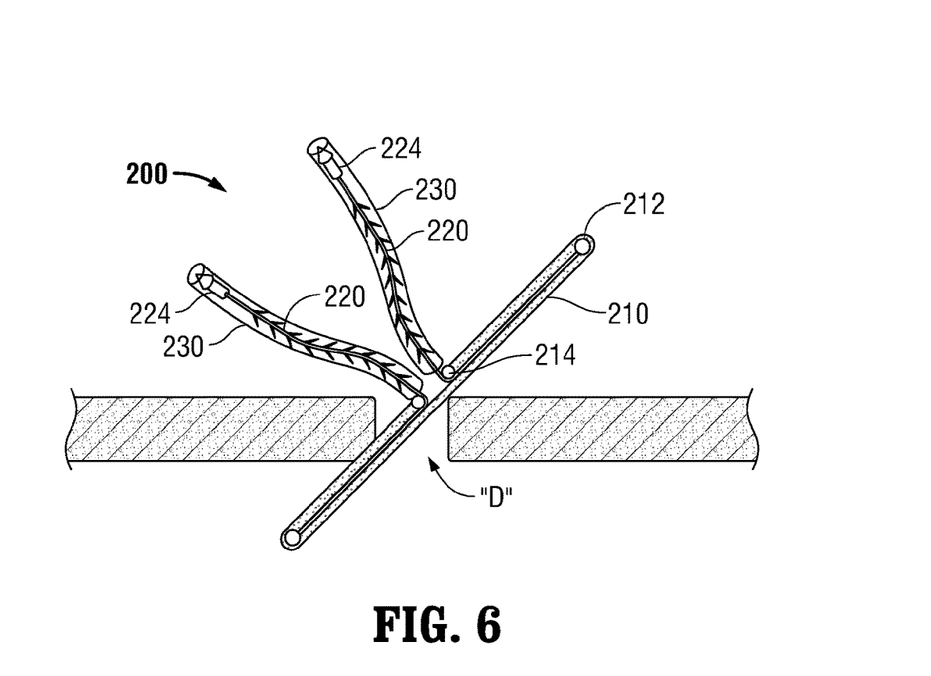
FIG. 6 is a side, cross-sectional view of the hernia repair device of FIG. 5 being inserted through a tissue defect.
Figure 7:
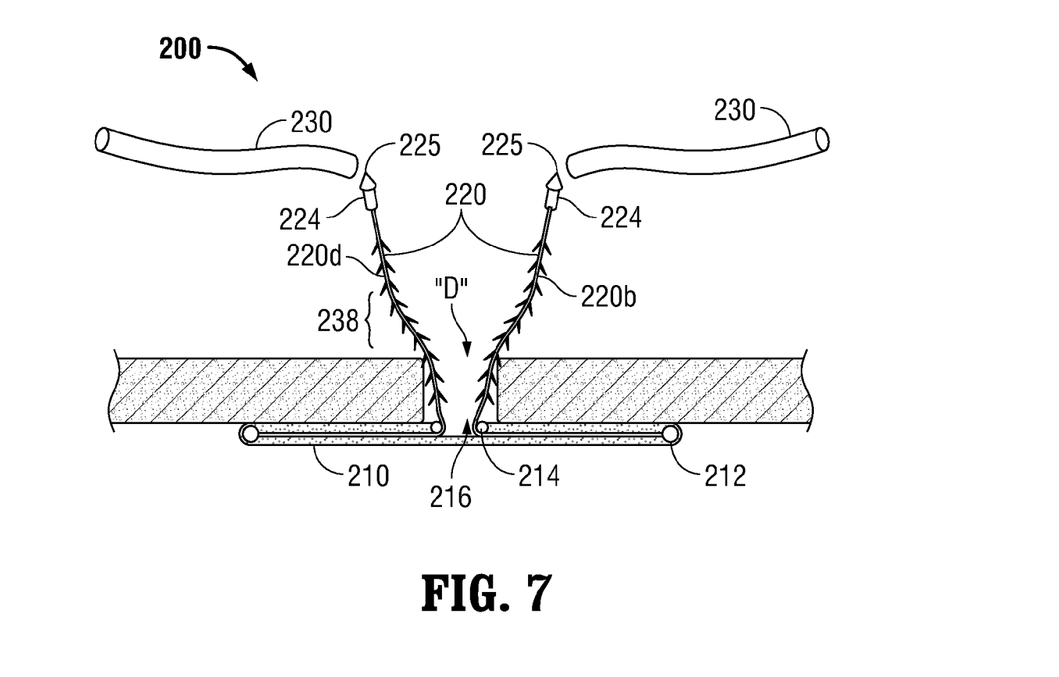
FIG. 7 is a side, cross-sectional view of the hernia repair device of FIG. 5 positioned within the tissue defect.
Figure 8:
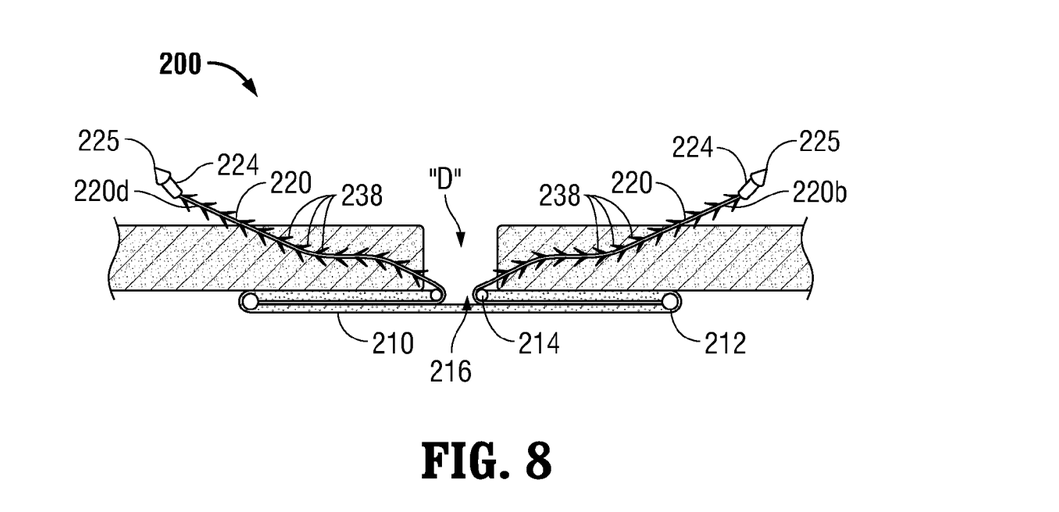
FIG. 8 is a side, cross-sectional view of the hernia repair device of FIG. 5 secured within tissue.

Referring now to FIGS. 1-3, one embodiment of a hernia repair device provided in accordance with the present disclosure is generally identified by reference numeral 100. Hernia repair device 100 includes a surgical mesh, or patch 110 and a plurality of filaments 120 coupled thereto. Mesh 110 defines a generally flat, circular configuration (although other configurations are contemplated) and is dimensioned to extend across a tissue defect "D" (FIGS. 6-8). It is envisioned that mesh 110 be flexible to conform to the anatomy of the defect "D" (FIGS. 6-8) and tissue surrounding the defect "D" (FIGS. 6-8). Mesh 110 may be formed from any suitable biomaterial, e.g., synthetic biomaterials or natural materials, including bioabsorbable and biodegradable materials.

Mesh 110 may also include at least one bioactive agent. The term "bioactive agent", as used herein, is used in its broadest sense and includes any substance or mixture of substances that have clinical use. A bioactive agent could be any agent that provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. For example, surgical mesh 110 may be coated with an anti-adhesive, e.g., on a distal surface thereof, to inhibit adhesion of mesh 110 to tissue and/or with a local anesthetic for temporary pain relief during implantation. It is envisioned that the bioactive agent may be applied to surgical mesh 110 in any suitable form of matter, e.g., films, powders, liquids, gels, combinations thereof, and the like.

With continued reference to FIGS. 1-3, mesh 110 may include one or more support members 112, 114 coupled thereto and configured to provide structural support and rigidity to mesh 110, while still allowing hernia repair device 100 to be manipulated during insertion and positioning of mesh 110 within a tissue defect "D" (FIGS. 6-8). Support member 112, for example, defines an annular configuration and is disposed at or near an outer periphery of mesh 110. Support member 112 may be formed from any suitable material, e.g., an absorbable or non-absorbable polymer. More specifically, support member 112 may be formed from a resiliently deformable material to facilitate insertion and positioning of mesh 110 within a tissue defect "D" (FIGS. 6-8) and to permit mesh 110 to conform to the contours of tissue surrounding the tissue defect "D" (FIGS. 6-8). Support member 112 may be adhered or otherwise engaged to mesh 110, e.g., on a proximal surface of mesh 110, or may be disposed at least partially within mesh 110. Further, support member 112 may be monolithically formed, or may be formed from woven strands of material.

Second annular support member 114 is radially centered relative to mesh 110 and is disposed about a central portion 116 thereof. Second support member 114 may be configured similarly to first support member 112. Alternatively, greater or fewer than two support members 112, 114 and/or support members of varying configuration may be provided to add structural support to mesh 110, although it is also envisioned that mesh 110 be configured to provide suitable support on its own, without the need for support member(s) 112, 114 coupled thereto. Further, filaments 120 may be configured to extend at least partially through portions of mesh 110, e.g., filaments 120 may be woven through mesh 110, to provide the necessary support (or further support) to mesh 110, or may simply extend along the proximal surface of mesh 110, as shown in FIGS. 4 and 5.

Each filament 120, as best shown in FIG. 1, defines an elongated configuration and is coupled to mesh 110 at a first end 122 thereof and to a needle 124 at a second end 126 thereof. Filaments 120 may be engaged to mesh 110 at radially symmetrical positions about mesh 110 or may be positioned relative to mesh 110 in any other suitable fashion and/or at any other position(s). Each filament 120 includes a plurality of barbs 128 disposed thereon and extending outwardly therefrom. Each barb 128 is configured to angle toward first end 122 of filament 120 such that, as can be appreciated, filaments 120 may be advanced through tissue in a first direction, e.g., lead by needle 124 disposed at second end 126 thereof, but are inhibited from being advanced through tissue in a second, opposite direction, e.g., toward mesh 110, due to the anchoring of barbs 128 within tissue. Filaments 120 may be formed from any suitable bio-compatible material, including metallic materials. Filaments 120 may be secured to or engaged within mesh 110 and/or support members 112, 114 in any suitable fashion, e.g., knotting, tying, welding, adhesion, etc.

With continued reference to FIGS. 1-3, needles 124 are coupled to second ends 126 of filaments 120. More specifically, needles 124 may be adhered, welded, knotted, or otherwise secured to filaments 120. Needles 124 each include a pointed tip 125 configured to facilitate passage of needles 124 through tissue with minimal trauma to surrounding tissue. Needles 124 may define curved configurations, substantially straight configurations (see FIGS. 4 and 6-8), or any other suitable configuration. The particular length and number of filaments 120 and/or the configuration of needles 124 may depend, for example, on the particular surgical procedure to be performed, anatomical considerations specific to the patient, or other factors.

Figure 4:
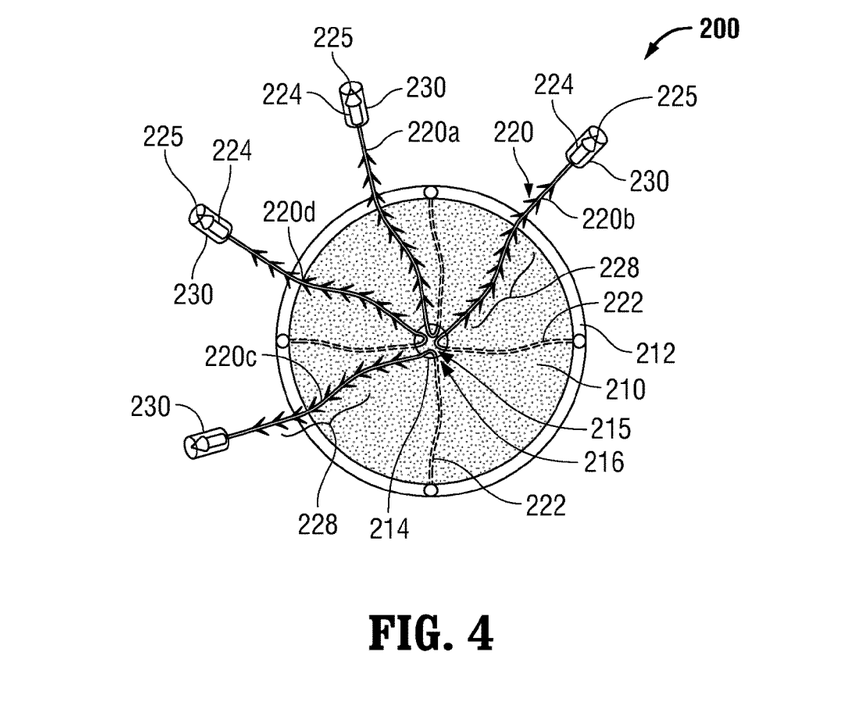
FIG. 4 is a top view of still another embodiment of a hernia repair device provided in accordance with the present disclosure.
Figure 5:
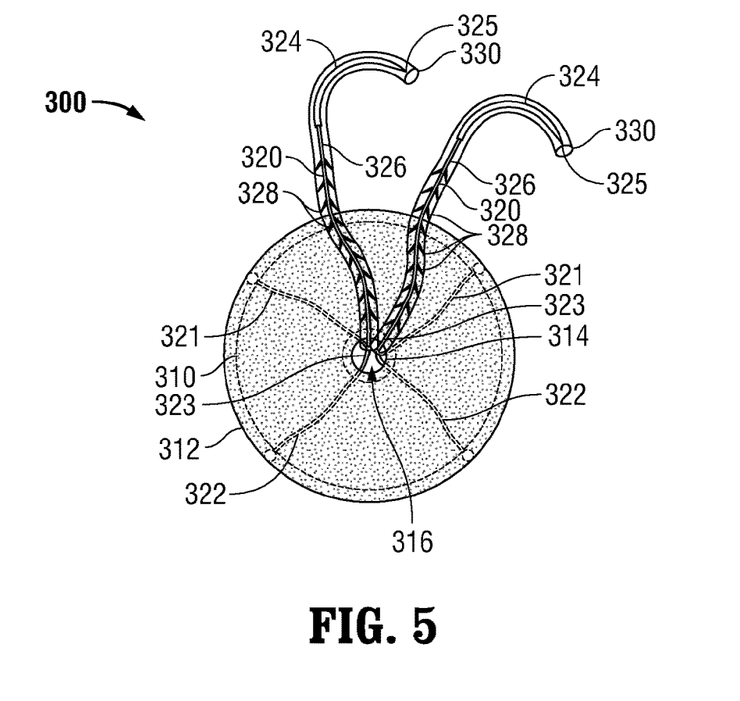
FIG. 5 is still yet another embodiment of a hernia repair device provided in accordance with the present disclosure.

Turning now to FIG. 4, another embodiment of a hernia repair device similar to hernia repair device 100 is shown generally identified by reference numeral 200. Hernia repair device 200 includes a mesh 210 having a first annular support member 212 disposed toward an outer periphery thereof and a second annular support member 214 positioned toward a central portion 216 of mesh 210. A plurality of filaments 220a-d (collectively filaments 220), e.g., four (4) filaments 220a-d, are coupled to first annular support member 212 at first ends 222 thereof and extend through second annular support members 214. More specifically, filaments 220 are engaged to first support member 212 at first ends 222 thereof, e.g., via looping, knotting, tying, welding, adhesion or other suitable securing mechanism, and extend substantially co-planarly along (or through, e.g., woven through) a proximal surface of mesh 210 radially inwardly toward central portion 216 of mesh 210. Filaments 220 extend into central portion 216 of mesh 210 and proximally through aperture 215 of second annular support member 214. As can be appreciated, in this configuration, filaments 220 provide radial structural support to mesh 210 in addition to the annular structural support provided by support members 212, 214.

Continuing with reference to FIG. 4, filaments 220a-d are radially symmetrically spaced about mesh 210, e.g., at 12 o'clock, 3 o'clock, 6 o'clock and 9 o'clock positions, respectively, although other configurations are contemplated. As can be appreciated, such a configuration permits mesh 210 to be maneuvered into position by manipulating one or more of filaments 220. For example, to draw hernia repair device 200 into approximation with tissue at the 12 o'clock position, the clinician would pull proximally on filament 200a (which is engaged to first support member 212 at the 12 o'clock position). In order to inhibit lateral movement during approximation, if desired, the clinician would simply retain filament 220c (which is disposed at the 6 o'clock position, opposite filament 220a).

With continued reference to FIG. 4, in this configuration, wherein filaments 220 are engaged radially about an outer periphery of mesh 210 and extend through central portion 216 of mesh 210, mesh 210 is more accurately manipulatable due to the equally-spaced distribution of filament attachment positions about the outer periphery of mesh 210, e.g., at the 12 o'clock, 3 o'clock, 6 o'clock and 9 o'clock positions. Further, in this configuration, mesh 210 is also more easily secured in position due to the fact that filaments 220 extend from central portion 216 of mesh 210 directly adjacent the tissue defect "D" (see FIGS. 6-8), reducing the likelihood that filaments 220 would catch, or interfere with mesh 210 or surrounding tissue and eliminating the need for the clinician to locate and retrieve each of the filaments 220 from within the surgical site. As can be appreciated, the diameter of second support member 214, through which filaments 220 extend, may depend on the size of the tissue defect "D" (FIGS. 6-8) or on other factors specific to the procedure to be performed. Hernia repair device 200 may otherwise be configured similarly to hernia repair device 100 (see FIGS. 1-3).

As shown in FIG. 4, similar to hernia repair device 100, each filament 220 of hernia repair device 200 includes a needle 224 disposed at a second end 226 thereof. Needles 224 are shown defining a substantially straight configuration although, as mentioned above, needles 224 may define any other suitable configuration, e.g., a curved configuration. A removable, protective sheath 230 is disposed about each of needles 224 to help avoid injury due to contact with pointed tips 225 of needles 224 as well as catching, or tearing of tissue, surgical materials and/or clothing during handling, preparation and insertion of hernia repair device 200. Protective sheaths 230 define generally tubular-shaped configurations and may be formed from any suitable bio-compatible material, e.g., polymeric materials. Sheaths 230 are configured to be retained on needles 224 despite rubbing, brushing, or other incidental contact, while also being capable of relatively easy removal from needles 224.

Continuing with reference to FIG. 4, each filament 220 includes a plurality of barbs 228 extending outwardly therefrom in a similar direction such that filaments 220 may be advanced through tissue in a first direction but are inhibited from retreating back through tissue in the opposite direction. Barbs 228 also allow incremental or ratcheting manipulation of hernia repair device 200 relative to surrounding tissue, as will be described in greater detail below. Further, sheaths 230 may define elongated configurations (see FIGS. 6-7) such that sheaths 230 cover needles 224 as well as the barbed portion of filaments 220, as will be described similarly hereinbelow with respect to sheaths 330 (FIG. 5). As can be appreciated, such a configuration protects against injury and damage during handling of hernia repair device 200. The use and operation of hernia repair device 200 will be described in greater detail hereinbelow with reference to FIGS. 6-8.

Turning now to FIG. 5, yet another embodiment of a hernia repair device provided in accordance with the present disclosure is shown generally identified by reference numeral 300. Hernia repair device 300 is similar to hernia repair devices 100, 200 (FIG. 4) and generally includes a mesh 310 supported by first and second annular support members 312, 314, and a pair of filaments 320 coupled thereto. Each of the filaments 320 is coupled to a plurality, e.g., two (2), support strands 321, 322 at a first end 323 thereof such that each filament 320 is ultimately coupled to first support member 312 at two spaced-apart positions. Accordingly, four (4) attachment positions for the filaments 320 about first support member 312 of mesh 310 are provided. The four attachment positions may be equally-spaced or otherwise configured. Greater or fewer than two (2) support strands 321, 322 for each filament 320 may alternatively be provided.

Each of the support strands 321, 322 of each filament 320 extends radially inwardly along, or through mesh 310. Support strands 321, 322 may be braided, wound, or otherwise attached to one another to form filaments 320, or filaments 320 may be tied, knotted, looped about, or otherwise secured to support strands 321, 322 adjacent central portion 316 of mesh 310. Support strands 321, 322 also provide structural support to mesh 310. Similarly as described above with respect to hernia repair device 200, filaments 320 of hernia repair device 300 extend proximally through second support member 314 positioned adjacent central portion 316 of mesh 310.

Continuing with reference to FIG. 5, each filament 320 includes a plurality of barbs 328 extending outwardly therefrom in a similar direction such that filaments 320 may be advanced through tissue in only one direction. Each filament 320 further includes a needle 324 disposed at a second end 326 thereof. Needles 324 may define any suitable configuration, e.g., a straightened configuration or a curved configuration. A removable, elongated protective sheath 330 is disposed about each of needles 324 and the barbed portions of filaments 320 to facilitate handling of hernia repair device, e.g., to help avoid injury or other damage due to contact with pointed tips 325 of needles 324 and/or barbs 328. Elongated protective sheaths 330 define tubular-shaped configurations and may be formed from any suitable bio-compatible material, e.g., polymeric materials. Further, it is envisioned that protective sheaths 330 define flexible configurations to facilitate manipulation of filaments 320 prior to removal of sheaths 330 therefrom. Sheaths 330 may be otherwise similarly configured to sheaths 230 of hernia repair device 200.

Turning now to FIGS. 6-8, the use and operation of hernia repair device 200 will be described. The use of hernia repair devices 100 and 300 are substantially similar to that of hernia repair device 200 and, thus, will not be described herein for purposes of brevity. Initially, with reference to FIG. 6, hernia repair device 200 is positioned adjacent the tissue defect "D" to be repaired. At this point, sheaths 230 remain disposed about the barbed portions of filaments 220 and needles 224 to inhibit accidental injury or damage during handling of hernia repair device 200.

With continued reference to FIGS. 6-8, and to FIG. 6 in particular, mesh 210 is manipulated such that mesh 210 is insertable through the tissue defect "D" with minimal trauma to the surrounding tissue. More specifically, due to the resiliently flexible configuration of support members 212, 214, mesh 210 is able to be bent, curved, or otherwise manipulated to facilitate passage of mesh 210 through the tissue defect "D." Once mesh 210 is positioned within the surgical site on a distal side of the tissue defect "D," mesh 210 may be released to allow mesh 210 to return to its initial state. In this position, sheaths 230 remain disposed over needles 224 and barbs 238 to protect against inadvertent injury and/or damage from pointed tips 225 of needles 224 and/or barbs 238.

As shown in FIG. 7, once moved into position, mesh 210 extends completely across the tissue defect "D" such that first support member 212 surrounds the tissue defect "D" and such that filaments 220 extend proximally through the defect "D." More specifically, filaments 220 extend proximally through second support member 214, which is positioned distal of and adjacent to the tissue defect "D." Due to the fact that filaments 220 extend through second support member 214, which is centrally disposed about mesh 210, mesh 210 is automatically centered relative to the tissue defect "D" by grasping filaments 220 collectively and pulling proximally. At this point, mesh 210 is ready to be manipulated into position and secured to tissue to repair the tissue defect "D." Accordingly, sheaths 230 may be removed from filaments 220 to expose needle 224 and barbs 238 in preparation for securing mesh 210 to tissue.

Turning now to FIGS. 7-8, in order to properly position and securely engage mesh 210 to tissue, filaments 220, lead by needles 224, are advanced proximally through tissue (see FIG. 8). As mentioned above, pointed tips 225 of needles 224 facilitate the passage of filaments 220 through tissue. Filaments 220 are selectively pulled through tissue to orient mesh 210 in the desired position. More specifically, due to the barbed configuration of filaments 220, as filaments 220 are pulled through tissue, retreat of filaments 220 back through tissue is inhibited by the engagement of barbs 238 within tissue. Thus, filaments 220 may be used to incrementally position mesh 210 in a ratchet-like fashion, as will be described below.

In order to secure mesh 210 in position adjacent the tissue defect "D", filament 220d, which is secured to mesh 210 at the 9 o'clock position is pulled through tissue proximally and toward the 9 o'clock position to move the section of mesh 210 adjacent the 9 o'clock position into approximation with a distal surface of tissue, while the other sections of mesh 210 remain relatively stationary. Upon release of filament 220d, mesh 210 is retained in position due to the engagement of barbs 238 within the tissue. In other words, barbs 238 inhibit mesh 210 from moving away from an approximated position relative to tissue. If it is decided that mesh 210 needs to be approximated further, the clinician may pull filament 220d further proximally to engage more of barbs 238 of filament 220d within tissue, thereby retaining mesh 210 in a further approximated position. In other words, advancing filament 220d a relatively small distance engages additional barbs 238 within tissue, retaining filament 220d in position. As such, the clinician may incrementally advance filament 220d (and the other filaments 220) to achieve the desired position of mesh 210 relative to tissue.

As best shown in FIG. 8, the filaments 220 are advanced proximally through tissue in a general direction toward the attachment position of that filament 220 to mesh 210. In other words, filament 220d is advanced proximally and in the 9 o'clock direction through tissue. As can be appreciated, such a configuration facilitates the accuracy of the incremental adjustments of filaments 220 to reposition mesh 210 relative to the defect "D" and automatically centers mesh 210 relative to the defect "D."

Once mesh 210 is positioned as desired at the 9 o'clock position, e.g., by manipulating filament 220d, as discussed above, filament 220b, which is secured to mesh 210 at the 3 o'clock position, is pulled proximally and toward the three o'clock position to move the section of mesh 210 adjacent the 3 o'clock position into approximation with the distal surface of tissue. It may be desired that filaments 220d, 220b be advanced different distances through tissue, for example, in instances where tissue adjacent the defect "D" defines a varying thickness, or where the defect "D" defines an asymmetrical configuration. This incremental and independent adjustment may then be repeated for each of the remaining filaments 220, e.g., filaments 220a and 220c, similarly as described above. Put more generally, the clinician may independently and incrementally pull each filament 220 through tissue to secure mesh 210 in a desired position despite various anatomical considerations, e.g., varied tissue thicknesses, varied defect configurations and/or various different tissue surface contours.

Once the filaments 220 have been advanced through tissue to the desired position, to approximate mesh 210 to tissue in the desired position, the proximal portions of filaments 220a-d including needles 224 may be cut, further stitched, or tied-off, leaving the remainder of filaments 220a-d fixedly secured within tissue. It is envisioned that the engagement of barbs 238 of filaments 220 within tissue in such a configuration as described above provides sufficient holding force to maintain mesh 210 in the desired position during the healing process of the tissue defect "D," obviating the need for additional fixation. However, additional fixation may be provided, if desired.

Hernia repair devices of the present disclosure may include a mesh configured to extend across a tissue defect and a plurality of filaments coupled to the mesh in proximity of an outer periphery thereof and extending from a central portion of the mesh. Each filament includes a plurality of barbs disposed along at least a portion of the length thereof and has a needle disposed at a free end thereof. In some embodiments, the mesh of the hernia repair device includes a first annular support member coupled thereto in proximity of the outer periphery thereof. In addition to the first annular support member, a second annular support member may be coupled to the mesh toward the central portion thereof.

In any of the presently disclosed embodiments, each filament may be coupled to the first annular support member and may extend radially inwardly along the mesh toward the second annular support member; each filament ultimately extending through an aperture defined by the second annular support member. The filaments may also be configured to provide radial structural support to the mesh, in addition to the support provided by the first and second annular support members. The filaments may also be equally-spaced about the mesh and relative to the first and second annular support members. Each filament may further include at least two support strands coupled thereto such that each filament is coupled to the mesh in at least two attachment positions.

In any of the presently disclosed embodiments, a removable protective sheath may be disposed about the needle of each of the filaments. The removable protective sheath of each filament is configured to extend along at least a portion of a length of the filament such that the removable protective sheath is disposed about barbs of the filament.

In any of the presently disclosed embodiments, the mesh may be resiliently deformable to facilitate insertion of the mesh through the tissue defect. The mesh may also be configured to conform to the anatomy of the tissue defect and surrounding tissue.

In any of the presently disclosed embodiments, the barbs of the filaments may be angled relative to the filaments such that each filament is configured to pass through tissue in a first direction but is inhibited from passing through tissue in a second, opposite direction.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A hernia repair device, comprising:
   a mesh defining a plane, an outer periphery, and a central portion, the mesh configured to extend across a tissue defect; and
   a plurality of filaments coupled to the mesh at a position spaced-apart from the central portion of the mesh, extending within the plane towards the central portion of the mesh, and extending out of the plane from the central portion of the mesh, each filament having a needle disposed at a free end thereof.

2. The hernia repair device according to claim 1, wherein each filament is coupled to the mesh in proximity of the outer periphery of the mesh.

3. The hernia repair device according to claim 1, wherein the mesh includes a first annular support member coupled thereto in proximity of the outer periphery thereof and a second annular support member coupled thereto in proximity of the central portion thereof.

4. The hernia repair device according to claim 3, wherein each filament is coupled to the first annular support member and extends radially inwardly within the plane toward the second annular support member, each filament extending out of the plane through an aperture defined by the second annular support member.

5. The hernia repair device according to claim 1, wherein the filaments are substantially equally-spaced about the mesh.

6. The hernia repair device according to claim 1, wherein each filament includes at least two support strands coupled thereto such that each filament is coupled to the mesh in at least two attachment positions.

7. The hernia repair device according to claim 1, further comprising a removable protective sheath disposed about the needle of each of the filaments.

8. A hernia repair device, comprising:
   a mesh defining a plane, an outer periphery, and a central portion, the mesh configured to extend across a tissue defect; and
   a plurality of filaments coupled to the mesh at a position spaced-apart from the central portion of the mesh, extending within the plane towards the central portion of the mesh, and extending out of the plane from the central portion of the mesh, each filament including a plurality of barbs disposed along at least a portion of the length thereof.

9. The hernia repair device according to claim 8, wherein each filament is coupled to the mesh in proximity of the outer periphery of the mesh.

10. The hernia repair device according to claim 8, wherein the mesh includes a first annular support member coupled thereto in proximity of the outer periphery thereof and a second annular support member coupled thereto in proximity of the central portion thereof.

11. The hernia repair device according to claim 10, wherein each filament is coupled to the first annular support member and extends radially inwardly within the plane toward the second annular support member, each filament extending out of the plane through an aperture defined by the second annular support member.

12. The hernia repair device according to claim 8, wherein each filament includes at least two support strands coupled thereto such that each filament is coupled to the mesh in at least two attachment positions.

13. The hernia repair device according to claim 8, further comprising a removable protective sheath disposed about at least a portion of a length of each of the filaments such that each removable protective sheath is disposed about barbs of the corresponding filament.

14. The hernia repair device according to claim 8, wherein the barbs are angled relative to the filaments such that each filament is configured to pass through tissue in a first direction but is inhibited from passing through tissue in a second, opposite direction.

15. A hernia repair device, comprising:
   a mesh defining a plane, an outer periphery, and a central portion, the mesh configured to extend across a tissue defect; and
   a plurality of filaments coupled to the mesh in proximity of the outer periphery of the mesh, extending within the plane towards the central portion of the mesh, and extending out of the plane from the central portion of the mesh.

16. The hernia repair device according to claim 15, wherein the mesh includes a first annular support member coupled thereto in proximity of the outer periphery thereof and a second annular support member coupled thereto in proximity of the central portion thereof.

17. The hernia repair device according to claim 16, wherein each filament is coupled to the first annular support member and extends radially inwardly within the plane toward the second annular support member, each filament extending out of the plane through an aperture defined by the second annular support member.

18. The hernia repair device according to claim 15, wherein the filaments are substantially equally-spaced about the mesh.

19. The hernia repair device according to claim 15, wherein each filament includes at least two support strands coupled thereto such that each filament is coupled to the mesh in at least two attachment positions.

* * * * *